United States Patent [19]

Delarge et al.

[11] 3,980,652

[45] Sept. 14, 1976

[54] 2-(4-METHYL-PIPERAZINO)-3 OR 5 CYANO PYRIDINE

[75] Inventors: Jacques E. Delarge, Dolembreux; Leopold N. Thunus, Liege; Charles Leon Lapière, Tongeren; André H. Georges, Ottignies, all of Belgium

[73] Assignee: A. Christiaens Societe Anonyme, Brussels, Belgium

[22] Filed: Sept. 26, 1975

[21] Appl. No.: 617,129

Related U.S. Application Data

[63] Continuation-in-part of Ser. No. 459,987, April 11, 1974, which is a continuation-in-part of Ser. No. 197,139, Nov. 9, 1971, Pat. No. 3,819,639.

[30] Foreign Application Priority Data

Nov. 11, 1970 United Kingdom............... 53675/70

[52] U.S. Cl............................. 260/268 H; 424/250
[51] Int. Cl.²...................................... C07D 401/04
[58] Field of Search................................ 260/268 H

[56] References Cited
UNITED STATES PATENTS 3,886,161   5/1975   Hardtmann..................... 260/268 H

OTHER PUBLICATIONS

Delarge et al. Chemical Abstracts vol. 77, 88325h, (1972).

*Primary Examiner*—Richard J. Gallagher
*Assistant Examiner*—Jose Tovar
*Attorney, Agent, or Firm*—Sughrue, Rothwell, Mion, Zinn and Macpeak

[57]   ABSTRACT

This invention relates to compounds of the formula

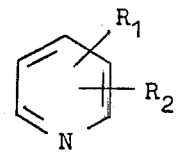

wherein $R_1$ in the 3- or 5-position is a cyano group whereas $R_2$ and in the 2-position is a N-methyl-piperazinyl group.

Said compounds may be used as anti-inflammatory and cardiovascular agents.

1 Claim, No Drawings

2-(4-METHYL-PIPERAZINO)-3 OR 5 CYANO PYRIDINE

CROSS RELATED APPLICATION

This application is a continuation-in-part of our earlier application Ser. No. 459,987, filed on Apr. 11, 1974, in turn a continuation-in-part of Ser. No. 197,139, filed Nov. 9, 1971, now U.S. Pat. No. 3,819,639.

BACKGROUND OF THE INVENTION

The present invention relates to new derivatives of pyridine having valuable pharmacological properties.

According to the present invention, there are provided compounds of formula:

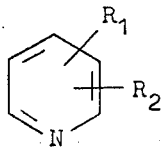

(I)

wherein $R_1$ in the 3- or 5-position of the pyridine nucleus represents a cyano group, whereas $R_2$ in the 2-position represents a N-methyl-piperazinyl group, as well as the pharmaceutically acceptable acid addition salts of the compounds of formula I.

A process for preparing said compounds of formula I comprises reacting a compound of formula:

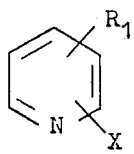

(II)

(wherein $R_1$ in the 3- or 5-position is as defined hereabove and X in the 2-position represents a halogen group) with N-methyl-piperazine.

The compounds of this invention may be converted, where possible, into their acid addition salts, preferably hydrochlorides, by conventional methods.

The compounds of this invention have interesting anti-inflammatory properties.

The anti-inflammatory properties are determined as follows:

The compounds to be tested are given as freshly prepared solutions or suspensions by oral route one hour before injecting the paw with carrageenan, a known inflammatory agent.

The inflammatory agent either in aqueous solution or suspension is then injected into the plantar tissue of the right hind paw of each rat, the left paw remaining untreated and serving as control. Each animal receives for example 0,05 ml of an aqueous solution containing 1% of carrageenan and 0,9% of sodium chloride.

4 hours after injection, the importance of swelling is determined by plethysmography and is expressed as a percent of the volume of the control paw.

The anti-inflammatory effect expressed as a percent of inhibition is obtained by comparison between rats treated with the anti-inflammatory agent and a control group of rats.

The results of the test for anti-inflammatory activity are given in table I.

TABLE 1

| Ref. No | Compound | Acute oedema induced by carrageenan % of inhibition |
|---|---|---|
| 128 | 2-(4'-methyl-1'-piperazinyl)-3-cyanopyridine | 63,2 |
| | Phenylbutazone | 41 |
| | Methiazinic acid | 46 |
| | Acetosalicylic acid | 0 |
| | Flufenamic acid | 34 |
| | Niflumic acid | 32 |

N.B. 100 mg/kg of anti-inflammatory agent are administered by oral route.

According to a further feature of the present invention, we thus provide pharmaceutical compositions comprising as active ingredient, at least one compound according to the present invention, together with a pharmaceutical carrier or excipient. The compositions are generally intended for peroral rectal or parenteral administration and also for external use. Pharmaceutical compositions for oral administration may, for example, be in the form of dosage units such as tablets, dragees or capsules in which at least one of the compounds according to the invention is mixed with a solid pharmaceutical carrier or excipient.

The compositions according to the present invention can also be used in the form of liquid preparations for oral administration especially syrups, elixirs, aqueous dispersions or solutions.

The compositions according to the present invention can also be in the form of solutions for parenteral administration. Solutions or suspensions for injections can be prepared by using, for example, distilled water in which at least one compound employed as active ingredient is dissolved or suspended, if desired, in the presence of a solubilizing agent.

The compositions according to the present invention may also be formulated for rectal administration, for example, the active ingredient in a suppository base.

The anti-inflammatory compositions according to this invention may also be applied for external use, for example, the active ingredient in an ointment base.

The compounds employed as active ingredients in the compositions according to the invention can be administered in varying doses depending on the particular compound being used, the condition of the patient, and the route of administration.

In general, however, the compounds can be administered orally or rectally in doses of from 50 to 1000 mg to be taken one to four times per day, or parenterally in a single dose of 20 to 500 mg per day.

DETAILED DESCRIPTION OF THE INVENTION

EXAMPLE 1

Preparation of 2-(4'-methyl-1'-piperazinyl)-3-cyanopyridine hydrochloride

The following mixture is placed into a 100 ml flask: 10 g of 2-chloro-3-cyanopyridine, 30 to 40 ml of toluene and 10 ml of 2-methylpiperazine. Said mixture is refluxed for 4 hours. The reaction mixture is evaporated under reduced pressure. The residue is taken up with water, rendered strongly alkaline with NaOH and extracted with $CHCl_3$. The extract is dehydrated and evaporated under reduced pressure to remove the excess of 1-methylpiperazine. The residue is then extracted with acetone and the product is precipitated as a dihydrochloride by passage of gaseous HCl through the acetone solution. Yield: 60%; m.p. 221°–222,5°C.

Elementary analysis: % Calculated: C; 55,46; H; 6,30; N; 23,48. % Found: C; 55,30; H; 6,53; N; 23,31.

EXAMPLE 2

Preparation of 2-(4'-methyl-1'-piperazinyl)-5-cyanopyridine

A mixture of 10 g of chlorinated starting compound of formula II, 30 to 40 ml of toluene and 10 g of N-methylpiperazine is heated and boiled under reflux conditions during 4 hours. After cooling, the solution thus obtained is evaporated under reduced pressure. 20 ml water and 20 ml NaOH (10%) are added and the resulting mixture is extracted with $CHCl_3$. The extraction solution is dried and then evaporated under reduced pressure. The residue is taken up with petroleum ether and stirred until it crystallizes. The solid product is filtered and then crystallized from petroleum ether.

| Melting point °C | Yield % | Analysis C | H | N |
|---|---|---|---|---|
| 61–62,5 | 75 | 65,34[1] | 6,93 | 27,72 |
| | | 65,05[2] | 7,12 | 27,61 |

[1] calculated
[2] found

EXAMPLE 3

| Dragees: | |
|---|---|
| Core: | |
| Compound of formula I | 50,0 mg |
| Colloidal silica | 5,0 mg |
| Lactose | 42,5 mg |
| Polyvidone | 3,5 mg |
| Glycerol | 0,5 mg |
| Maize starch | 8,0 mg |
| Talc | 10,0 mg |
| Magnesium stearate | 0,5 mg |
| Coating: | |
| Gum lac | 2,0 mg |
| Gum arabic | 5,4 mg |
| New-Coccine | 0,1 mg |
| Talc | 13,0 mg |
| Colloidal silica | 9,5 mg |
| Saccharose | 50,0 mg |
| | for one dragee |

EXAMPLE 4

| Tablets: | |
|---|---|
| Core: | |
| Compound of formula I | 200,0 mg |
| Colloidal silica | 17,0 mg |
| Stearic acid | 4,0 mg |
| Gelatine | 4,0 mg |
| Glycerol | 1,6 mg |
| Maize starch | 52,0 mg |
| Magnesium stearate | 1,4 mg |
| | for one tablet |

EXAMPLE 5

| Capsules: | |
|---|---|
| Compound of formula I | 100,0 mg |
| Lactose | 120,0 mg |
| Rice starch | 30,0 mg |
| Maize starch | 30,0 mg |
| Magnesium stearate | 5,0 mg |
| Gelatine } envelope | 78,0 mg |
| Tartrazine } | 0,2 mg |
| | for one capsule |

EXAMPLE 6

| Suppositories: | |
|---|---|
| Compound of formula I | 300 mg |
| Witepsol H 12 mass ( ) | 600 mg |
| | for one suppository |

( ) a mixture of triglycerides and partial glycerides of saturated fatty acids ($C_{12}$-$C_{18}$) originating from plants, furnished by Dynamit Nobel AG, Köln-Mülheim, Western Germany.

EXAMPLE 7

| Vials: | |
|---|---|
| Compound of formula I | 20,0 mg |
| Natrium chloride | 85,0 mg |
| Distilled water to form | 10,0 ml |
| | for one vial |

What we claim is:
1. A compound of the formula:

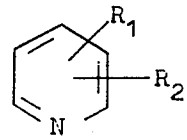

(I)

wherein $R_1$ in the 3- or 5-position of the pyridine nucleus represents the cyano group, wherein $R_2$ in the 2-position represents N-methyl-piperazino or the pharmaceutically acceptable acid addition salts thereof.

* * * * *